(12) United States Patent
Govari

(10) Patent No.: US 11,089,947 B2
(45) Date of Patent: Aug. 17, 2021

(54) CATHETER WITH IRRIGATOR AND/OR ASPIRATOR AND WITH FIBER-OPTIC BRAIN-CLOT ANALYZER

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 68 days.

(21) Appl. No.: 16/192,156

(22) Filed: Nov. 15, 2018

(65) Prior Publication Data

US 2020/0154984 A1 May 21, 2020

(51) Int. Cl.
*A61B 1/00* (2006.01)
*A61B 1/015* (2006.01)
(Continued)

(52) U.S. Cl.
CPC ...... *A61B 1/00165* (2013.01); *A61B 1/00087* (2013.01); *A61B 1/00142* (2013.01);
(Continued)

(58) Field of Classification Search
CPC ............... G01N 33/86; G01N 33/6896; G01N 33/4905; G01N 33/6893; A61N 7/00;
(Continued)

(56) References Cited

U.S. PATENT DOCUMENTS 5,690,117 A    11/1997   Gilbert
5,752,513 A *   5/1998   Acker ...................... A61B 5/06
                                                                                128/899
(Continued)

FOREIGN PATENT DOCUMENTS

WO    2014099905 A1   6/2014
WO    2017216645 A2   12/2017
(Continued)

OTHER PUBLICATIONS

U.S. Appl. No. 16/057,189, filed Aug. 7, 2018, entitled "Brain Clot Characterization Using Optical Signal Analysis, and Corresponding Stent Selection."
(Continued)

*Primary Examiner* — Manuel A Mendez
(74) *Attorney, Agent, or Firm* — Troutman Pepper Hamilton Sanders LLP

(57) ABSTRACT

A medical system includes a probe, an electrooptical measurement unit, a processor and a treatment unit. The probe, which is configured for insertion into a blood vessel of a brain, includes (a) one or more optical fibers configured to guide an optical signal to interact with a brain clot in the blood vessel, and to output the optical signal that interacted with the brain clot, and (b) a channel selected from a group of channels consisting of an irrigation channel and an aspiration channel. The electrooptical measurement unit is configured to collect and measure the outputted optical signal. The processor is configured to identify a composition of the brain clot by analyzing the measured optical signal from the probe. The treatment unit is configured to provide treatment, selected from the group of treatments consisting of dissolving the brain clot by irrigation and aspiring the brain clot through the channel.

6 Claims, 3 Drawing Sheets

(51) Int. Cl.
*A61B 1/05* (2006.01)
*A61B 1/06* (2006.01)
*A61B 8/08* (2006.01)
*A61B 17/00* (2006.01)
*A61M 1/00* (2006.01)

(52) U.S. Cl.
CPC ................ *A61B 1/015* (2013.01); *A61B 1/05* (2013.01); *A61B 1/0607* (2013.01); *A61B 8/5238* (2013.01); *A61B 2017/00292* (2013.01); *A61M 1/0031* (2013.01)

(58) Field of Classification Search
CPC .............. A61B 17/22; A61B 17/22012; A61B 18/1492; A61B 5/031; A61K 38/49; A61K 38/4846; C12Q 1/56
See application file for complete search history.

(56) References Cited

U.S. PATENT DOCUMENTS

| | | | |
|---|---|---|---|
| 6,660,013 | B2 | 12/2003 | Rabiner et al. |
| 6,997,871 | B2 | 2/2006 | Sonnenschein et al. |
| 2007/0167681 | A1 | 7/2007 | Gill et al. |
| 2017/0189040 | A1 | 7/2017 | Anand et al. |
| 2017/0265879 | A1* | 9/2017 | Washburn, II ....... A61B 1/0002 |

FOREIGN PATENT DOCUMENTS

| | | | | |
|---|---|---|---|---|
| WO | WO-2017216645 | A2 * | 12/2017 | ......... A61B 18/1477 |
| WO | 2018137949 | A1 | 8/2018 | |

OTHER PUBLICATIONS

U.S. Appl. No. 62/675,952, filed May 24, 2018, entitled "Position Sensor on Brain Clot Sheath and Location Pad Collar."
U.S. Appl. No. 15/674,380, filed Aug. 10, 2017, entitled "ENT Image Registration."
Scott L. Diamond: "Engineering Design of Optimal Strategies for Blood Clot Dissolution", Annual Review of Biomedical Engineering, vol. 1, No. 1, Aug. 1, 1999.
EP 19209075.1-1115—Extended European Search Report dated Jan. 2, 2020.

* cited by examiner

CATHETER WITH IRRIGATOR AND/OR ASPIRATOR AND WITH FIBER-OPTIC BRAIN-CLOT ANALYZER

FIELD OF THE INVENTION

The present invention relates generally to invasive medical probes, and particularly to catheters for cerebrovascular applications.

BACKGROUND OF THE INVENTION

Various types of medical probes include mechanical and optical elements. For example, U.S. Pat. No. 5,690,117 describes a rigid ultrasonic-fiberoptic stylet situated within a modified intracranial Silastic catheter and allows indirect and direct real time visualization through the tip of the catheter. The ultrasonic portion of the stylet allows the surgeon to correctly aim the stylet and catheter towards a brain ventricle by giving the surgeon a two-dimensional echogram view of the ventricle and allows the surgeon to maintain the proper trajectory or path towards the anterior horn of the lateral ventricle as the stylet and catheter are passed through the brain. The fiberoptic portion of the stylet allows the surgeon to directly view the interior of the anterior horn of lateral ventricle once the ventricle is punctured. An irrigation port may be provided in addition to or in place of one of the illuminating fibers to allow clearing of the distal optics by infusing sterile saline.

As another example, U.S. Pat. No. 6,660,013 describes a method and apparatus for removing plaque, fatty deposits, and other occlusions from blood vessels using ultrasonic energy. The method and apparatus have particular application in removing plaque from the carotid artery in a nonthermal manner. The apparatus is designed to have as small a cross-sectional profile as possible, therefore allowing the apparatus to be used in a minimally-invasive manner. An ultrasonic probe may include aspiration channels on its outer surface. The probe of the present invention is particularly amenable, because of its small size, to the use of a flexible fiberoptic viewing device. In some embodiments, means of irrigation and aspiration are provided, in the form of small holes or fenestrations drilled along the length of the probe.

U.S. Pat. No. 6,997,871 describes an endoscope which comprises a sheath, an articulation section adjacent to its distal tip, and two or more separate optical channels that produce two or more distinct views. Each of the optical channels comprises an objective lens and a means of capturing and/or viewing the image. The objective lens or lenses of the optical channel that produces the first distinct view, is located at a first location on the distal tip. The objective lens or lenses of the optical channel that produces the second distinct view is located at a second location on the proximal end of the articulation section or on the sheath of the endoscope adjacent to or located proximally of the articulation section. In an embodiment, a channel for suction or irrigation is provided, as well as illumination fibers.

U.S. Patent Application Publication 2007/0167681 describes a portable system and method for performing endoscopic procedures. A portable display device, such as a laptop computer, is coupled to a handle comprising a miniature camera and fiber optic illumination subsystem. A sterile disposable portion is fitted over the illumination subsystem and inserted into a target area on a patient. Images of the target area are conveyed from the camera to the display device while an endoscopic procedure is performed, thus facilitating real-time diagnosis during the procedure. In a preferred embodiment, the endoscope has a fiber optic waveguide that transmits an image from a distal end to a proximal end. A lens system is positioned at the distal end of the fiber optic waveguide. The probe can include an open channel in either the sheath or the imaging probe to provide for the insertion of other operative elements to flush the site with fluid, direct light or other energy source onto a treatment site, or to remove a tissue sample.

SUMMARY OF THE INVENTION

An embodiment of the present invention provides a medical system including a probe, an electrooptical measurement unit, a processor and a treatment unit. The probe, which is configured for insertion into a blood vessel of a brain, includes (a) one or more optical fibers configured to guide an optical signal to interact with a brain clot in the blood vessel, and to output the optical signal that interacted with the brain clot, and (b) a channel selected from a group of channels consisting of an irrigation channel and an aspiration channel. The electrooptical measurement unit is configured to collect and measure the outputted optical signal. The processor is configured to identify a composition of the brain clot by analyzing the measured optical signal from the probe. The treatment unit is configured to provide treatment, selected from the group of treatments consisting of dissolving the brain clot by irrigation and aspiring the brain clot through the channel.

In some embodiments, the processor is configured to identify, based on the measured optical signal, whether the brain clot is dissolvable by the group of treatments consisting of dissolving the brain clot by irrigation and aspiring.

In some embodiments, the processor is configured to output a recommendation for selecting a brain-clot removal method that matches the composition of the brain clot.

There is additionally provided, in accordance with an embodiment of the present invention, a method including guiding an optical signal via one or more optical fibers in a probe that is inserted into a blood vessel of a brain, to interact with a brain clot in the blood vessel. An outputted optical signal that interacted with the brain clot is collected from the probe and measured. A composition of the brain clot is identified by a processor analyzing the measured optical signal from the probe. The brain clot is removed by at least one treatment, selected from the group of treatments consisting of irrigating the brain clot and applying suction to aspirate the brain clot, using one or more channels in the probe.

The present invention will be more fully understood from the following detailed description of the embodiments thereof, taken together with the drawings in which:

DETAILED DESCRIPTION OF EMBODIMENTS

Overview

An ischemic stroke, typically caused by an obstructing clot in a large blood vessel of the brain, is an emergency medical condition. The location of the clot in the brain may be detected by computerized tomography (CT) or fluoroscopy imaging. Typically, however, such imaging cannot identify the material composition of a clot, nor to indicate whether the clot is accessible with an immediately available clot treatment tool.

Clot composition may vary, for example, from a preponderance of old red blood cells (typically making the clot relatively solid and hard) to a preponderance of fresh blood cells, or of white blood cells, either of which typically form a relatively gel-like and pliable clot. Accordingly, based on identifying clot composition using a probe, one or more from a variety of treatments may be selected to remove the clot, yet, as noted above, typically these may not be readily available in situ.

Embodiments of the present invention that are described hereinafter provide systems, probes, and methods for identification of soft and/or fresh clots by optical analysis, and for dissolving and/or aspirating such clots. The disclosed probes comprise one or more working channels coupled to an irrigation/aspiration (I/A) treatment unit, configured to dissolve the clot by irrigation, and/or remove it by suction aspiration.

In some embodiments, an optical fiber is incorporated into a shaft of a probe, such as a catheter, to guide an optical signal to interact with the clot to determine its composition. The optical fiber is coupled at its proximal end to an electro-optical measurement unit, which collects and measures the optical signals generated by the fiber that has interacted with the clot, digitizes the measured signal, and outputs the digital signal to a processor for analysis to identify the material composition of the clot. In some embodiments, the processor is further configured to output a recommendation for selecting a brain clot removal method, such as irrigation and/or aspiration, or another method that matches the composition of the brain clot.

A system and method for the analysis and identification of the composition of a brain clot to indicate clot characteristics is described in U.S. patent application Ser. No. 16/057,189, filed Aug. 7, 2018, entitled "Brain Clot Characterization Using Optical Signal Analysis, and Corresponding Stent Selection," which is assigned to the assignee of the present patent application and whose disclosure is incorporated herein by reference.

The disclosed probes, which are capable of treating a fresh clot by irrigation and/or aspiration, in addition to identifying clot type, may enable a physician to remove a clot in a prompt manner. By doing so, the disclosed systems, probes, and methods for diagnosis and treatment of a stroke may improve the clinical outcome of the required emergency medical clot-removal catheterization procedure.

System Description

Figure 1A:
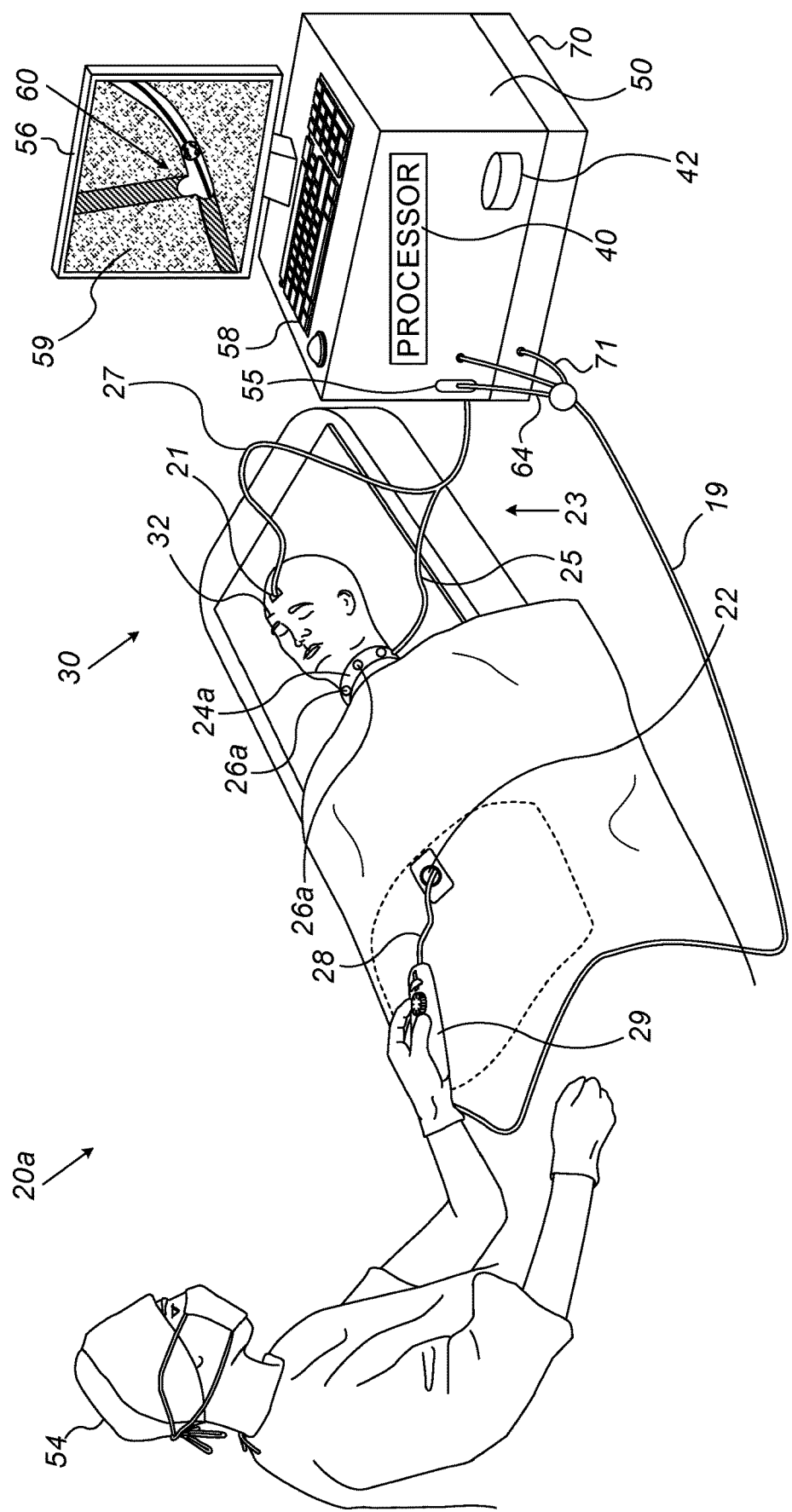
FIGS. 1A and 1B are schematic, pictorial illustrations of catheter-based clot composition analysis and removal systems, in accordance with embodiments of the present invention.
Figure 1B:
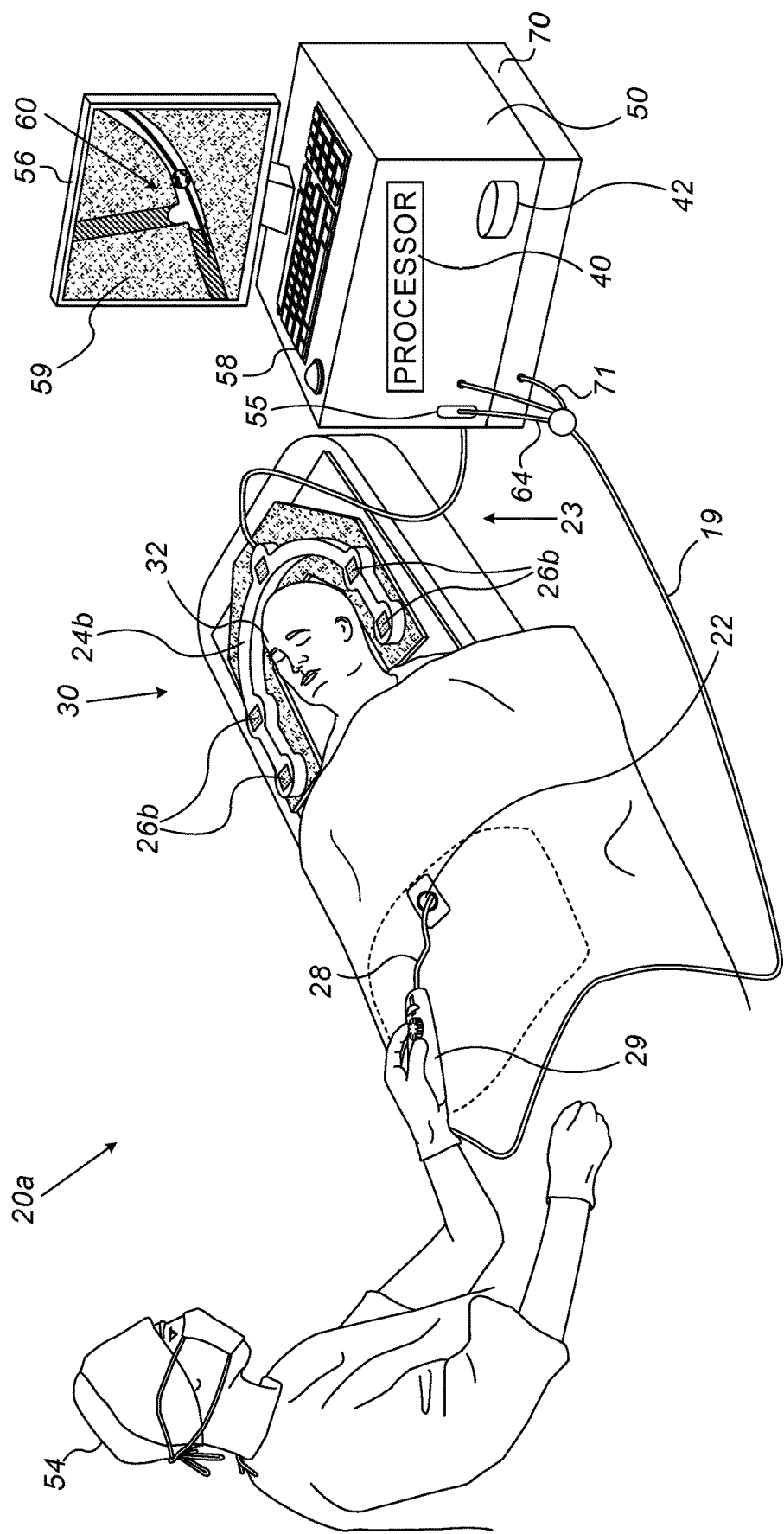

FIGS. 1A and 1B are schematic, pictorial illustrations of catheter-based clot composition analysis and removal systems 20a and 20b, in accordance with embodiments of the present invention.

In some embodiments, prior to performing the catherization procedure, CT images of a patient 22 are acquired. The CT images are stored in a memory 42 for subsequent retrieval by a processor 40. The processor uses the images to present, for example, brain section image 59 demonstrating a clot on a display 56. During the disclosed catheterization procedure, systems 20a and 20b register a position of a distal end of a catheter 28 inside the patient's brain, with frames of reference of brain images of patient 32, herein assumed by way of example to comprise real-time fluoroscopic images. The position of a catheter distal end is tracked using a magnetic tracking sub-system 23, which tracks spatial coordinates of a magnetic sensor fitted at the distal end.

Magnetic tracking sub-system 23 of system 20a, shown in FIG. 1A, comprises a location pad 24a, which is implemented as a collar around the neck of patient 32. By putting location pad 24a around the neck, location pad 24a is configured to automatically compensate for patient head movement. Location pad 24a comprises magnetic field radiators 26a which are fixed in positions relative to the head of patient 32 and which transmit alternating sinusoidal magnetic fields into a region 30 where the head of patient 32 is located. A console 50 electrically drives radiators 26a via a cable 25. In an embodiment, further compensation of head motion is provided by attaching a reference sensor 21 to the patient's forehead. Console 50 is configured to receive signals from reference sensor 21 via a cable 27. A location tracking system that comprises a neck collar location pad is described in U.S. Provisional Patent Application 62/675,952, filed May 24, 2018, entitled "Position Sensor on Brain Clot Sheath and Location Pad Collar," which is assigned to the assignee of the present patent application and whose disclosure is incorporated herein by reference.

Physician 54, operating system 20a, holds catheter controller handle 29, which is connected to the proximal end of catheter 28. Controller 29 allows the physician to advance and navigate catheter 28 in the brain, for example, through an entry point 22 at an artery at a thigh of patient 32. Using magnetic position tracking sub-system 23, a physician 54 advances the distal end of catheter 28 to the clot through blood vessels, usually arteries, so as to enable diagnosis of the type of clot and optionally to perform a corresponding invasive therapeutic procedure to remove the clot. Console 50 receives the position signals from the magnetic position sensor fitted at the distal end of catheter 28 via a cable 19 that connects to catheter 28 via handle 29.

Elements of system 20a, including radiators 26a, are controlled by a system processor 40, comprising a processing unit communicating with one or more memories. Processor 40 may be mounted in console 50, which comprises operating controls 58 that typically include a keypad and/or a pointing device such as a mouse or trackball. Physician 54 uses operating controls on handle 29 to interact with the processor while performing the registration of system 20a. During the registration process, an image 59 of a brain section is presented on display 56. Subsequent to the registration process described above, physician 54 uses the operating controls to advance the distal end of catheter 28 to a brain location where a clot is blocking an artery. The processor presents results of the catheter tracking procedure on display 56.

Processor 40 uses software stored in a memory 42 to operate system 20a. The software may be downloaded to processor 40 in electronic form, over a network, for example, or it may, alternatively or additionally, be provided and/or stored on non-transitory tangible media, such as magnetic, optical, or electronic memory. In particular, processor 40 runs a dedicated algorithm that enables processor 40 to perform the disclosed steps, as described below.

In some embodiments, an electro-optical measurement unit 55 is included in console 50. Electro-optical measurement unit 55 is configured to collect and measure an optical signal output from a fiber optic 64, which is included in catheter 28, as described below, and runs in cable 19 to console 50. Electro-optical measurement unit 55 then conveys the measured signal to processor 40. Based on analyzing the measured signal, processor 40 identifies the composition of a clot, as further elaborated below. In some embodiments, the processor presents the identified clot composition on display 56.

In some embodiments of the present invention, an Irrigation/Aspiration (I/A) treatment unit 70 is included in console 50. I/A treatment unit 70 is configured to pump irrigation fluid and/or to apply suction (e.g., by a pump that creates sub-pressure inside channel 71) through a channel 71, which is formed in catheter 28, as described below, and which runs in cable 19 to console 50.

System 20b, shown in FIG. 1B, has a different magnetic location pad design, namely a location pad 24b. As seen, location pad 24b is fixed to the bed, and irradiators 26b surround a patient headrest horizontally. In this example, system 20b lacks reference sensor 21, and therefore the head of the patient must be harnessed to keep it motionless. Other components of system 20b are generally identical to those of system 20a. A location tracking system using a location pad similar to location pad 24b is described in U.S. patent application Ser. No. 15/674,380, filed Aug. 10, 2017, entitled "ENT Image Registration," which is assigned to the assignee of the present patent application and whose disclosure is incorporated herein by reference.

Systems 20a and 20b shown in FIGS. 1A and 1B are chosen purely for the sake of conceptual clarity. Other system elements may be included, for example additional controls on handle 29 for controlling the diagnostic tooling designed to determine clot type. CARTO® magnetic tracking systems, which track a location and orientation of a magnetic position sensor in an organ of a body using techniques similar to those applied by systems 20a and 20b, are produced by Biosense-Webster.

Figure 2:
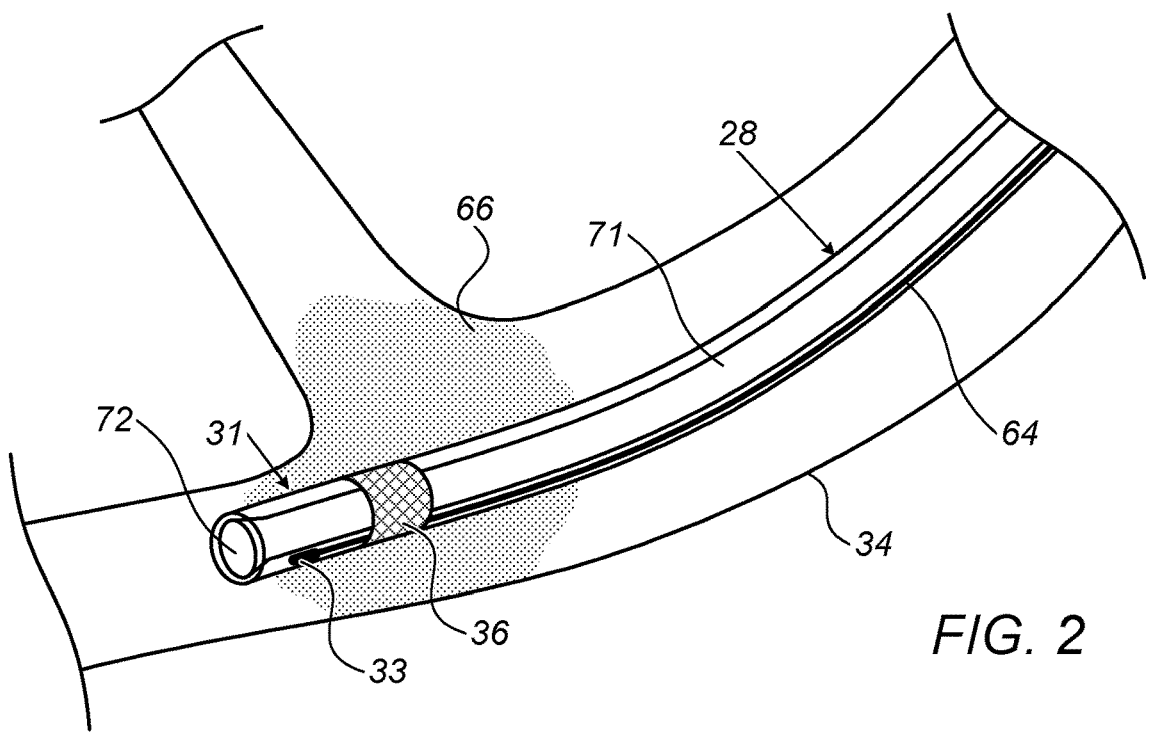
FIG. 2 is a schematic cross-sectional view of a brain clot and a catheter, in accordance with an embodiment of the present invention.

Catheter with Irrigator and/or Aspirator and with Fiberoptic Brain-Clot Analyzer FIG. 2 is a schematic cross-sectional view of a brain clot 66 and a catheter 28, in accordance with an embodiment of the present invention. As seen, clot 66 blocks blood flow in an artery 34, where, in some embodiments, physician 54 navigates and advances catheter 28 distally in artery 34, to a location beyond clot 66.

A distal end 31 of catheter 28 comprises a magnetic position sensor 36, which is used for tracking distal end 31 in the brain to assist in navigating distal end 31 to clot 66. A system and method for tracking catheter 28 and have it engaging (e.g., penetrating or traversing) clot 66 are described in the above cited U.S. Provisional Patent Application 62/675,952.

In some embodiments, catheter 28 comprises an optical fiber 64 to guide an optical signal. Electro-optical measurement unit 55 (shown in FIGS. 1A and 1B) couples the proximal edge of fiber 64, and collects and measures the diagnostic optical signal output from fiber 64, and further conveys the measured signal to processor 40. The processor analyzes the conveyed measured signals to identify the composition of clot 66. In the context of the present patent application and in the claims, the term "composition of a clot" refers to various chemical, biological, and/or physical characteristics of the clot and/or the elements making-up the clot.

An optical device 33, in the form of, for example, either a narrow band-stop reflection Bragg grating or a wide-band mirror, is disposed at the distal edge of fiber 64. Using device 33, an incident light double-passes clot 66 and is subsequently analyzed by unit 55. A system and method for brain clot 66 characterization using optical signal analysis are described in the above cited U.S. patent application Ser. No. 16/057,189.

In some embodiments, catheter 28 comprises a working channel 71 having a channel-opening 72. Channel 71, which is coupled at its proximal end to I/A treatment unit 70 (shown in FIGS. 1A and 1B), is used for dissolving and/or aspiration removal of the clot, if a clot composition measurement and analysis, as described above, confirms that these means are suitable to treat the identified clot. In the event that the optical measurement and subsequent analysis indicates otherwise, for example, that the clot is too dense for aspiration, a different tool may be inserted via working channel 71 into clotted blood vessel 34, such as a clot removal stent.

The example illustration shown in FIG. 2 is chosen purely for the sake of conceptual clarity. For example, in another embodiment, channel-opening 72 is located on a perimeter (i.e., at a side wall, or transversally) of catheter 28 rather than on a distal edge opening of the catheter.

Figure 3:
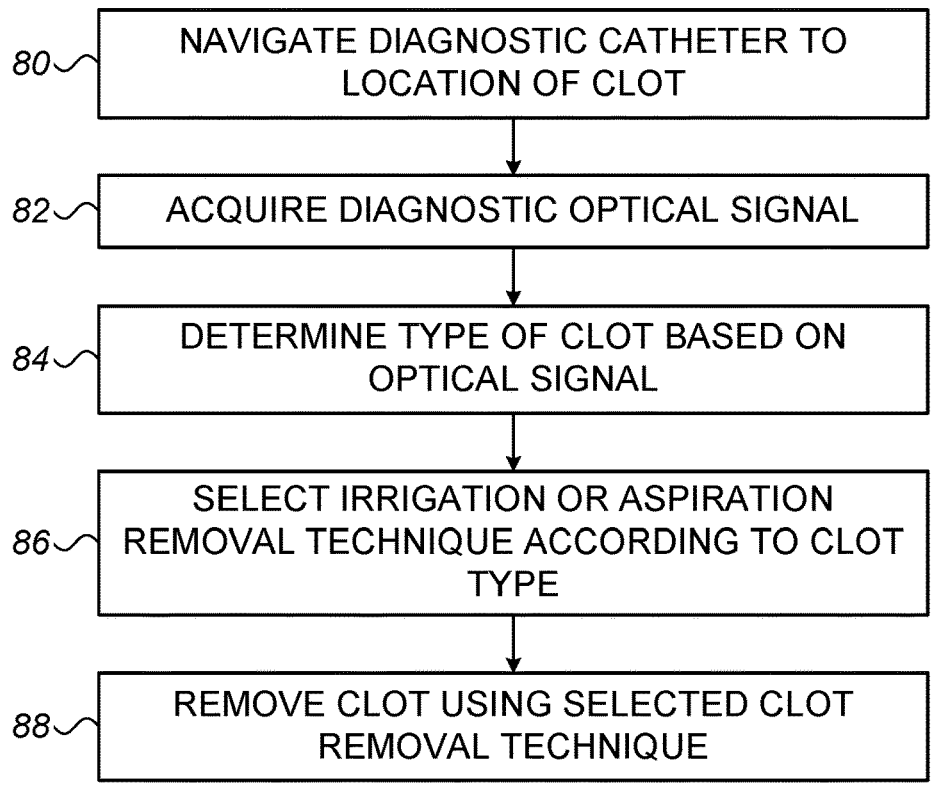
FIG. 3 is a flow chart that schematically illustrates a method for clot composition analysis, and subsequent selection of clot removal method, in accordance with an embodiment of the present invention.

FIG. 3 is a flow chart that schematically illustrates a method for clot composition analysis, and subsequent selection of clot removal method, in accordance with an embodiment of the present invention. The process begins with physician 54 navigating catheter 28 to traverse clot 66 with the catheter distal end, at a navigation step 80. Next, physician 54 operates an optical sensing system, comprising an optical device in catheter 28, to measure an optical signal indicative of clot 66 composition, at a signal acquisition step 82.

Next, processor 40 analyzes the measured signals, so as to identify the composition of clot 66 (i.e., type of clot), at a clot analysis step 84.

Next, based on the identified composition of clot 66, which processor 40 may present to physician 54 on display 56, physician 54 selects a best suited clot removal technique for removing clot 66 from the brain of patient 32, at a removal technique selection step 86. In some embodiments, physician 54 selects to dissolve and/or aspire clot 66. Finally, physician 54 removes clot 66 using the selected brain clot removal technique, at a clot removal step 88.

The example flow chart shown in FIG. 4 is chosen purely for the sake of conceptual clarity. In alternative embodiments, for example, based on the indication from processor 40, physician 54 may choose to remove the clot by a clot removal stent that physician 54 inserts through working channel 71.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical system, comprising:
   a catheter having a proximal end and a distal end;
   a magnetic position sensor located at the distal end of the catheter to track the distal end of the catheter in a blood vessel of a brain to navigate the distal end of the catheter to a brain clot in the blood vessel;
   a one or more optical fibers disposed within the catheter configured to guide an optical signal to interact with the brain clot in the blood vessel, and to output the optical signal that interacted with the brain clot; and
   a channel selected from a group of channels consisting of an irrigation channel and an aspiration channel;
   an electrooptical measurement unit, configured to collect and measure the outputted optical signal;
   a processor, configured to identify a composition of the brain clot by analyzing the measured optical signal from the probe; and
   a treatment unit, which is configured to provide treatment, selected from the group of treatments consisting of dissolving the brain clot by irrigation and aspiring the brain clot through the channel.

2. The medical system according to claim 1, wherein the processor is configured to identify, based on the measured optical signal, whether the brain clot is dissolvable by the group of treatments consisting of dissolving the brain clot by irrigation and aspiring.

3. The medical system according to claim 1, wherein the processor is configured to output a recommendation for selecting a brain-clot removal method that matches the composition of the brain clot.

4. A method, comprising:
   providing a catheter having a proximal end and a distal end;
   placing a magnetic position sensor at the distal end of the catheter;
   tracking the distal end of the catheter in a blood vessel of a brain to navigate the distal end of the catheter to a brain clot in the blood vessel;
   guiding an optical signal via one or more optical fibers in the catheter that is inserted into the blood vessel, to interact with the brain clot in the blood vessel;
   collecting from the probe and measuring an outputted optical signal that interacted with the brain clot;
   in a processor, identifying a composition of the brain clot by analyzing the measured optical signal from the probe; and
   removing the brain clot by at least one treatment, selected from the group of treatments consisting of irrigating the brain clot and applying suction to aspirate the brain clot, using one or more channels in the probe.

5. The method according to claim 4, wherein identifying the composition of the brain clot comprises identifying whether the brain clot is dissolvable by the group of treatments consisting of dissolving the brain clot by irrigation and aspiring.

6. The method according to claim 4, and comprising outputting, by the processor, a recommendation for selecting a brain-clot removal method that matches the composition of the brain clot.

* * * * *